(12) United States Patent
Takahashi et al.

(10) Patent No.: US 8,105,493 B2
(45) Date of Patent: Jan. 31, 2012

(54) AGGREGATION AND DISPERSION METHODS OF MAGNETIC PARTICLES, SEPARATION AND DETECTION METHODS USING THE SAME AND DETECTION KIT

(75) Inventors: Yuki Takahashi, Chiba (JP); Noriyuki Ohnishi, Chiba (JP); Xiaomao Xie, Chiba (JP)

(73) Assignee: JNC Corporation, Tokyo (JP)

( * ) Notice: Subject to any disclaimer, the term of this patent is extended or adjusted under 35 U.S.C. 154(b) by 883 days.

(21) Appl. No.: 12/147,216

(22) Filed: Jun. 26, 2008

(65) Prior Publication Data
US 2009/0001025 A1  Jan. 1, 2009

(30) Foreign Application Priority Data

Jun. 29, 2007 (JP) ................................. 2007-173469
Feb. 8, 2008 (JP) ................................. 2008-028641

(51) Int. Cl.
*B03C 1/01* (2006.01)
*H01F 1/00* (2006.01)

(52) U.S. Cl. ........ 210/695; 210/222; 436/526; 428/407; 252/62.51 R; 252/62.53; 252/62.54; 252/62.56; 209/232

(58) Field of Classification Search .................. 436/526; 428/407; 252/62.51 R, 62.53, 62.56, 62.54; 210/222, 695; 209/232
See application file for complete search history.

(56) References Cited

U.S. PATENT DOCUMENTS
2010/0207051 A1* 8/2010 Fonnum et al. ........ 252/62.51 R FOREIGN PATENT DOCUMENTS
| EP | 2 009 044 A1 | 12/2008 |
| JP | 2004-201648 | 7/2004 |
| JP | 2005-082538 | 3/2005 |

OTHER PUBLICATIONS

H. Furukawa et al., "Affinity selection of target cells from cell surface displayed libraries: a novel procedure using thermo-responsive magnetic nanoparticles" Applied Microbiology and Biotechnology, Springer Verlag, Berlin, DE, vol. 62, No. 5-6, Oct. 1, 2003, pp. 478-483.

Akihiko Kondo et al., "Development and application of thermosensitive magnetic immunomicrospheres for antibody purification" Applied Microbiology Biotechnology, 1994, pp. 99-105.

Akihiko Kondo et al., "Preparation of Thermo-Sensitive Magnetic Hydrogel Microspheres and Application to Enzyme Immobilization" Journal of Fermentation and Bioengineering, vol. 84, No. 4, 1997, pp. 337-341.

* cited by examiner

*Primary Examiner* — David A Reifsnyder
(74) *Attorney, Agent, or Firm* — J.C. Patents (57) ABSTRACT

It is intended to provide a method capable of simply aggregating magnetic particles having a surface modified with a thermoresponsive polymer at a given temperature without heating or cooling an aqueous solution containing the magnetic particles, and a separation method and a detection method of a substance to be detected in a sample using the method. The method of separating a substance to be detected from a sample includes the steps of: mixing an adsorbent and the sample in an aqueous solution to adsorb the substance to be detected on the adsorbent, aggregating the adsorbent by changing a salt concentration in the aqueous solution; and collecting the adsorbent from the aqueous solution by a magnetic force, wherein said adsorbent comprises a magnetic particle of an average particle size of 50 to 1000 nm, a surface of which is modified with a thermoresponsive polymer and is immobilized with a substance having an affinity for the substance to be detected.

11 Claims, 1 Drawing Sheet

AGGREGATION AND DISPERSION METHODS OF MAGNETIC PARTICLES, SEPARATION AND DETECTION METHODS USING THE SAME AND DETECTION KIT

CROSS-REFERENCE TO RELATED APPLICATION

This application claims the priority benefit of Japanese applications serial no. JP2007-173469, filed Jun. 29, 2007 and no. JP2008-028641, filed Feb. 8, 2008. All disclosure of the Japanese applications is incorporated herein by reference.

BACKGROUND OF THE INVENTION

1. Field of the Invention

The present invention relates to aggregation and dispersion methods of magnetic particles, separation and detection methods using the same and a detection kit.

2. Background Art

As a method of collecting a substance to be detected (also referred to as a target substance) in a mixed liquid (sample), a method in which microparticles on which a ligand capable of specifically adsorbing a substance to be detected has been immobilized are added to a sample thereby adsorbing the substance to be detected on the microparticles, thereafter, the microparticles are collected, and the substance to be detected is separated and collected from the microparticles is known. In particular, magnetic particles have a feature that they can be easily collected by a magnet, therefore, they are used as a means for efficiently collecting a substance to be detected. When the particle size of magnetic particles is more than 500 nm, the magnetic particles are easy to be magnetically collected, however, the adsorption reaction rate between the ligand on the surface of magnetic particles and the substance to be detected is not sufficient. On the contrary, when the particle size is 200 nm or less, though the adsorption reaction rate is high, the magnetic particles are difficult to be magnetically collected, and thus the substance to be detected cannot be collected.

Appl. Microbiol. Biotechnol., vol. 41, pp. 99-105, 1994 (Non-patent document 1) and Journal of Fermentation and Bioengineering, vol. 84, pp. 337-341, 1997 (Non-patent document 2) disclose stimulus-responsive magnetic particles (magnetic particles having a surface modified with a stimulus-responsive polymer) obtained by subjecting magnetic particles having a particle size of about 100 to 200 nm to surface modification with polyisopropyl acrylamide having a lower critical solution temperature (hereinafter sometimes referred to as "LCST").

The magnetic particles having a surface modified with a stimulus-responsive polymer have a particle size of about 100 to 200 nm and are very small, therefore they are well dispersed in water, but cannot be magnetically collected in a dispersed state. However, in the case where an aqueous solution of magnetic particles having a surface modified with a thermoresponsive polymer is heated and the temperature thereof is raised to a temperature not lower than the LCST, the magnetic particles having a surface modified with a thermoresponsive polymer are deposited and aggregated. Since this aggregate can be easily collected by a magnetic force, an attempt has been made to perform separation of various biomolecules or microorganisms in a sample using the magnetic particles having a surface modified with the thermoresponsive polymer and is immobilized with an antibody or an antigen (an adsorbent).

However, in the case where collection is carried out using such a method, a heating and cooling system is required for raising the temperature of a sample containing the adsorbent using a magnetic particle having a surface modified with a thermoresponsive polymer to a temperature not lower than the LCST by heating thereby to aggregate or magnetically collect the adsorbent. Further, in the case where the adsorbent is applied to an immunodiagnostic system or the like for measuring a large variety of analytical items in a short time, a heating and cooling operation is required, therefore, the procedure is complicated. Further, in order to further reduce the time for analysis and measurement, a method of more promptly performing redispersion after once aggregating the adsorbent has also been demanded.

SUMMARY OF THE INVENTION

Accordingly, an object of the present invention is to provide a method capable of simply aggregating magnetic particles having a surface modified with a thermoresponsive polymer at a given temperature without heating or cooling an aqueous solution containing an adsorbent and a sample, and a separation method and a detection method of a substance to be detected in a sample using the method. Further, another object of the present invention is to provide a method of redispersing the adsorbent in a short time.

The present inventors made intensive studies in order to achieve the above object, and as a result, they found that by changing a salt concentration in an aqueous solution containing magnetic particles having a surface modified with a thermoresponsive polymer, the magnetic particles can be aggregated and dispersed, and thus the present invention has been completed based on this finding.

That is, the gist of the present invention is as follows.

[1] A method of separating a substance to be detected in a sample, comprising the steps of:

mixing an adsorbent and the sample in an aqueous solution to adsorb the substance to be detected on the adsorbent, aggregating the adsorbent by changing a salt concentration in the aqueous solution; and collecting the adsorbent from the aqueous solution by a magnetic force, wherein said adsorbent comprises a magnetic particle of an average particle size of 50 to 1000 nm, a surface of which is modified with a thermoresponsive polymer and is immobilized with a substance having an affinity for the substance to be detected.

[2] The method according to [1], wherein the thermoresponsive polymer is a polymer obtained by polymerization of at least one type of monomer selected from the group consisting of N-n-propylacrylamide, N-isopropylacrylamide, N-t-butylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine and N-methacryloylmorpholine.

[3] The method according to [1], wherein the thermoresponsive polymer is a polymer obtained by polymerization of at least one type of monomer selected from the group consisting of N-acryloylglycinamide, N-acryloylnipecotamide and N-acryloylasparaginamide.

[4] The method according to anyone of [1] to [3], wherein the average particle size of the magnetic particle is from 50 to 200 nm.

[5] The method according to any one of [1] to [4], wherein the salt contains at least one type of compound selected from the group consisting of lithium sulfate, sodium sulfate, potassium sulfate, magnesium sulfate, ammonium sulfate, sodium carbonate and potassium carbonate.

[6] The method according to any one of [1] to [4], wherein the salt contains at least one type of compound selected from the group consisting of a sodium monocarboxylate, a potassium monocarboxylate, a sodium dicarboxylate, a potassium dicarboxylate, a sodium tricarboxylate, a potassium tricarboxylate, a sodium tetracarboxylate and a potassium tetracarboxylate.

[7] The method according to [6], wherein the salt contains at least one type of compound selected from the group consisting of sodium acetate, sodium aspartate, disodium citrate, disodium ethylenediamine tetraacetate, sodium glutamate, sodium iminodiacetate, sodium maleate, sodium malonate, sodium oxalate, disodium succinate and sodium tartrate.

[8] A kit for separating or detecting a substance to be detected in a sample, comprising an adsorbent and an aqueous salt solution, wherein said adsorbent comprises a magnetic particle of an average particle size of 50 to 1000 nm, a surface of which is modified with a thermoresponsive polymer and is immobilized with a substance having an affinity for the substance to be detected.

[9] A method of aggregating or dispersing magnetic particles, comprising the step of aggregating or dispersing magnetic particles having a surface modified with a thermoresponsive polymer, which are obtained by subjecting magnetic particles to surface modification with a thermoresponsive polymer, by changing a salt concentration in an aqueous solution.

[10] The method according to [9], wherein the magnetic particle having a surface modified with a thermoresponsive polymer has a substance having an affinity for a substance to be detected on its surface.

[11] A method of detecting a substance to be detected in a sample, comprising the steps of: separating the substance to be detected from the sample by adsorbing the substance to be detected on the adsorbent by the method according to any one of [1] to [7]; and detecting the substance to be detected adsorbed on the adsorbent.

By using the aggregation and dispersion method of the present invention and the separation method or detection method of a substance to be detected in a sample to which this method is applied, magnetic particles having a surface modified with a thermoresponsive polymer and an adsorbent using such magnetic particles can be aggregated simply at a given temperature without heating or cooling an aqueous solution containing the adsorbent and the sample, and this aggregated adsorbent can be magnetically collected, thereby the substance to be detected can be separated or detected. In particular, it is advantageous to apply such an adsorbent to an immunodiagnostic system or the like for measuring a large variety of analytical items in a short time. Further, prompt separation or detection of a substance to be detected in a sample can be achieved.

DETAILED DESCRIPTION OF THE INVENTION

Hereinafter, the present invention will be described in detail.

The present invention is directed to an aggregation and dispersion method of magnetic particles having a surface modified with a thermoresponsive polymer or an adsorbent, in which the magnetic particles having a surface modified with a thermoresponsive polymer or the adsorbent is aggregated and dispersed by changing a salt concentration in an aqueous solution.

(Magnetic Particle Having a Surface Modified with Thermoresponsive Polymer)

The magnetic particle having a surface modified with a thermoresponsive polymer to be used in the present invention is a particle which is obtained by subjecting a magnetic particle to surface modification with a thermoresponsive polymer. The "surface modification" refers to a state in which a thermoresponsive polymer has been directly or indirectly and chemically immobilized on the surface of a magnetic particle, or a state in which a thermoresponsive polymer has been directly or indirectly entangled on the surface of a magnetic particle. Here, the term "indirectly" refers to a state in which the surface modification of a magnetic particle with a thermoresponsive polymer is achieved via another substance (for example, a polyhydric alcohol such as dextran).

The magnetic particle to be used in the present invention may be a particle formed of iron oxide or ferrite, and for example, may be a particle formed of iron oxide, ferrite or magnetite and another inorganic substance or organic substance, such as a particle formed of a polyhydric alcohol and magnetite. The thermoresponsive polymer may be immobilized (for surface modification) on iron oxide, ferrite, magnetite or the like, or, may be immobilized on a polyhydric alcohol or a polyhydric alcohol derivative, which is a component of the magnetic particle.

The average particle size of the magnetic particle having a surface modified with a thermoresponsive polymer is generally from 50 to 1000 nm, and preferably from 80 to 200 nm.

(Magnetic Particle)

The magnetic particle to be used for the magnetic particle having a surface modified with a thermoresponsive polymer can be produced by the method disclosed in, for example, JP-T-2002-517085. That is, the method is a method in which an aqueous solution containing an iron(II) compound, or an iron(II) compound and a metal (II) compound is placed under an oxidative condition necessary for forming a magnetic oxide, the pH of the solution is maintained at 7 or higher, whereby a magnetic nanoparticle of iron oxide or ferrite is formed. Further, the magnetic particle can also be produced by mixing an aqueous solution containing a metal(II) compound and an aqueous solution containing iron(III) under an alkaline condition.

Alternatively, the magnetic particle can also be produced from a polyhydric alcohol and magnetite. As the polyhydric alcohol, any can be used without particular limitation as long as it is an alcohol which has at least two hydroxy groups as its constituent units and can bind to an iron ion. Examples of the polyhydric alcohol include dextran, polyvinyl alcohol, mannitol, sorbitol, cyclodextrin and the like. A method for producing a magnetic particle using dextran is disclosed in, for example, JP-A-2005-082538, and the magnetic particle can also be produced by this method. Further, a compound which has an epoxy group and is capable of forming a polyhydric alcohol structure after ring opening such as a glycidyl methacrylate polymer can also be used.

The magnetic particle to be used in the present invention preferably has an average particle size of less than 1000 nm so as to have a favorable dispersibility after being subjected to surface modification with a thermoresponsive polymer. In particular, in order to increase the adsorption reaction rate between a substance having an affinity for a substance to be detected which is immobilized on the thermoresponsive polymer-modified surface of the magnetic particle and the substance to be detected, the average particle size thereof is preferably less than 200 nm. In order to increase the magnetic collection rate of the magnetic particle having a surface modified with a thermoresponsive polymer, the magnetic particle preferably has an average particle size of 30 nm or more, more preferably 40 nm or more.

(Thermoresponsive Polymer)

The thermoresponsive polymer to be used in the present invention is a polymer which changes its structure in response to a change in temperature, which enables the control of aggregation and dispersion. As the thermoresponsive polymer, there are a polymer having an upper critical solution temperature (hereinafter sometimes referred to as "UCST") and a polymer having a lower critical solution temperature (hereinafter sometimes referred to as "LCST"), and from the viewpoint of operability or the like, a polymer having an LCST can be more preferably used.

Examples of the polymer having an LCST include polymers obtained by polymerization of at least one type of monomer selected from the group consisting of N-substituted (meth)acrylamide derivatives such as N-n-propylacrylamide, N-isopropylacrylamide, N-t-butylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine and N-methacryloylmorpholine; polyoxyethylene alkylamine derivatives such as hydroxypropyl cellulose, partially oxidized polyvinyl alcohol, polyvinyl methyl ether, a (polyoxyethylene-polyoxypropylene) block copolymer and polyoxyethylene laurylamine; polyoxyethylene sorbitan ester derivatives such as polyoxyethylene sorbitan laurate; (polyoxyethylene alkylphenyl ether) (meth)acrylates such as (polyoxyethylene nonylphenyl ether) acrylate and (polyoxyethylene octylphenyl ether) methacrylate; polyoxyethylene (meth)acrylic acid ester derivatives including (polyoxyethylene alkyl ether) (meth)acrylates such as (polyoxyethylene lauryl ether) acrylate and (polyoxyethylene oleyl ether) (meth)acrylate and the like (hereinafter referred to as an "LCST-type polymer").

As the thermoresponsive polymer, the above-mentioned LCST-type polymer can be used. Also, a polymer obtained by copolymerization by further adding a monomer such as acrylamide, acetylacrylamide, biotinol acrylate, N-biotinyl-N'-methacryloyltrimethyleneamide (it is also possible to form a monomer by binding a substance other than biotin), acryloylsarcosinamide, methacryloylsarcosinamide, acryloylmethyluracil or acryloylglutaminamide to a monomer constituting the above-mentioned LCST-type polymer can also be used. In general, the content of such a monomer constituting the LCST-type polymer in the polymer is 90 mol % or more of the content of total monomers constituting the polymer.

In particular, as the thermoresponsive polymer, a polymer obtained by polymerization of at least one type of monomer selected from the group consisting of N-n-propylacrylamide, N-isopropylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine and N-methacryloylmorpholine can be preferably used.

In the present invention, a polymer obtained by polymerization of N-isopropylacrylamide can be further more preferably used.

As the polymer having a UCST, a homopolymer or a copolymer obtained by polymerization of at least one type of monomer selected from the group consisting of acryloylglycinamide, acryloylnipecotamide and acryloylasparaginamide (hereinafter referred to as a "UCST-type polymer") can be exemplified.

As the thermoresponsive polymer, the above-mentioned UCST-type polymer can be used. Further, a polymer obtained by polymerization of acrylamide, acetylacrylamide, biotinol acrylate, N-biotinyl-N'-methacryloyltrimethyleneamide (it is also possible to form a monomer by binding a substance other than biotin), acryloylsarcosinamide, methacryloylsarcosinamide, acryloylmethyluracil, acryloylglutaminamide or the like can be used as the above-mentioned UCST-type polymer. In general, the content of such a monomer constituting the UCST-type polymer in the polymer is 90 mol % or more of the content of total monomers constituting the polymer.

In both of the LCST-type polymer and the UCST-type polymer, the LCST or UCST can be controlled by changing the type of monomer to be polymerized or copolymerized or a ratio thereof, therefore, it is possible to design a polymer in accordance with the operating temperature.

The degree of polymerization of the thermoresponsive polymer that can be suitably used in the present invention is generally from 50 to 10000.

As for a method for producing the thermoresponsive polymer, the thermoresponsive polymer can be obtained by dissolving the above-mentioned monomer in an organic solvent or water, replacing the system with an inert gas, raising the temperature to a polymerization temperature, adding an azo-based polymerization initiator such as azobisisobutylonitrile or a peroxide such as benzoyl peroxide in the case of an organic solvent, a polymerization initiator such as ammonium persulfate, potassium persulfate, 2,2'-azobis(2-amidinopropane) dihydrochloride or 4,4'-azobis (4-cyanovalerate) in the case of an aqueous system, and continuing heating with stirring. Thereafter, also purification of the thus produced polymer can be carried out by a method in which reprecipitation is carried out in a poor solvent and a deposited polymer is filtered, or a method in which stimulation of temperature change to cause aggregation of polymer is given to aggregate the polymer and the aggregated polymer is separated by centrifugation.

The binding between the magnetic particle and the thermoresponsive polymer can be achieved by a method well known in this technical field (for example, a method described in ADV. Polym. Sci., vol. 4, p. 111, 1965, or J. Polymer Sci., Part-A, 3, p. 1031, 1965) such as a method in which binding is achieved through a reactive functional group, or a method in which a polymerizable unsaturated bond is introduced into an active hydrogen of the polyhydric alcohol in the magnetic particle or the polyhydric alcohol, and graft polymerization is carried out between the thermoresponsive polymer and the magnetic particle. In this way, the magnetic particle having a surface modified with the thermoresponsive polymer can be obtained. A magnetic particle having a surface modified with a thermoresponsive polymer obtained by subjecting a magnetic particle to surface modification using an LCST-type polymer as the thermoresponsive polymer is sometimes referred to as an "LCST-type magnetic particle". In the same manner, a magnetic polymer having a surface modified with a thermoresponsive polymer obtained by subjecting a magnetic particle to surface modification using a UCST-type polymer as the thermoresponsive polymer is sometimes referred to as a "UCST-type magnetic particle".

The thickness of a layer of the thermoresponsive polymer to be used for surface modification of the magnetic particle is preferably from 1 to 100 nm, more preferably from 5 to 50 nm.

(Adsorbent)

The adsorbent to be used in the present invention is a particle, obtained by immobilizing a substance (ligand) having an affinity for a substance to be detected on a thermoresponsive polymer-modified surface of the magnetic particle.

Since the adsorbent of the present invention has a substance (ligand) having an affinity for a substance to be detected on the surface of the magnetic particle, it specifically adsorbs the substance to be detected which specifically interacts with the ligand. In the case where the substance to be detected is a protein, by immobilizing biotin, avidin, glutathione, lectin, an antibody or the like as the substance having an affinity for the substance to be detected on the surface of the magnetic particle and labeling the protein with the counterpart of such a substance, specific adsorption of the protein can be achieved. In the case of biotin, by immobilizing avidin, a biotinylated protein to be detected can be adsorbed via a specific binding to avidin, or a biotinylated antibody is adsorbed, which is then used for further adsorbing antigens against the antibody. In the present invention, commercially available avidin or a biotinylated protein can be used, and biotinylation can be performed in accordance with a method well known in this technical field. In the case of glutathione, specific adsorption of a protein containing glutathione S-transferase (hereinafter referred to as "GST") can be achieved. The preparation of such a GST-containing protein can be performed in accordance with a method well known in this technical field.

As a method of immobilizing a ligand to a thermoresponsive polymer-modified surface of the magnetic particle, a method of binding an antibody to a thermoresponsive polymer will be described. As disclosed in WO 01/009141, an addition polymerizable monomer is formed by binding biotin to a polymerizable functional group such as a methacryl group or an acryl group and the resulting addition polymerizable monomer is copolymerized with another monomer, whereby biotin can be bound to a thermoresponsive polymer. On the other hand, avidin is bound to an antibody as a ligand, and the resulting conjugate is mixed with a biotin-bound thermoresponsive polymer, whereby the antibody can be adsorbed on the thermoresponsive polymer by utilizing the binding between avidin and biotin. In the case where glutathione is used in place of biotin, glutathione S-transferase may be used in place of avidin. Further, when the polymer is produced, a monomer having a functional group such as a carboxyl group, an amino group or an epoxy group may be copolymerized with another monomer, and then a substance having an affinity for an antibody (for example, Melon Gel, Protein A, Protein G or the like) may be bound to the resulting polymer via this functional group in accordance with a method well known in this technical field. By binding an antibody as a ligand to the thus obtained substance having an affinity for the antibody, the antibody can be bound to the thermoresponsive polymer.

In this way, a thermoresponsive polymer bound to a ligand can be obtained. Such a thermoresponsive polymer bound to a ligand can be separated and purified by placing it under a condition in which the thermoresponsive polymer aggregates, followed by centrifugation or the like. Further, in the case where a thermoresponsive polymer has been immobilized on the surface of a magnetic particle, by collecting the magnetic particle with a magnet, purification thereof can be achieved.

(Method of Magnetic Collection)

The magnetic force of a magnet or the like to be used for collection of the magnetic particles having a surface modified with a thermoresponsive polymer or the adsorbent varies depending on the magnitude of the magnetic force of the magnetic particles to be used or the like. As the magnetic force, a magnetic force of a magnitude capable of collecting target magnetic particles can be suitably used. As a material of the magnet, for example, Neodymium Magnet manufactured by Magna Co., Ltd. can be used. As described above, in the present invention, the magnetic particles having a surface modified with a thermoresponsive polymer, the adsorbent or the like are collected by a magnetic force of a magnet or the like. Since a thermoresponsive polymer has been immobilized on the surface of the magnetic particles, magnetic particles with a nanometer size, which are difficult to be collected in a dispersed state, are intentionally aggregated, whereby the collection ratio thereof can be increased. In the present invention, aggregation or dispersion of such magnetic particles having a surface modified with a thermoresponsive polymer, adsorbent or the like can be achieved by changing a salt concentration in an aqueous solution. Accordingly, in the present invention, such an adsorbent is simply aggregated and magnetically collected at a given temperature without heating or cooling an aqueous solution containing the adsorbent and a sample, and a substance to be detected in the sample can be separated or detected.

(Aggregation and Dispersion Method of the Present Invention)

In the present invention, aggregation and dispersion of the magnetic particles having a surface modified with a thermoresponsive polymer, the adsorbent or the like can be achieved by changing a salt concentration in an aqueous solution.

A preferred concentration of the magnetic particles having a surface modified with a thermoresponsive polymer or the adsorbent in an aqueous solution (after a salt is added) varies depending on the substance to be detected, type of magnetic particles having a surface modified with a thermoresponsive polymer or the like, however, from the viewpoint of operability or the like, it is generally in the range of from 0.1 to 10 mg/mL.

The salt to be used in the present invention is not particularly limited as long as it can exhibit the effect of the present invention, and examples thereof include sulfates such as lithium sulfate, sodium sulfate, potassium sulfate, magnesium sulfate and ammonium sulfate; halides such as sodium chloride, potassium chloride, magnesium chloride, calcium chloride and barium chloride; nitrates such as magnesium nitrate and calcium nitrate; thiocyanates such as potassium thiocyanate; carbonates such as sodium carbonate and potassium carbonate; borates; phosphates and the like. These salts can be used alone or by combining two or more types thereof.

Further, as the salt to be used in the present invention, organic acid salts including sodium monocarboxylates such as sodium acetate; sodium dicarboxylates such as sodium aspartate, sodium glutamate, sodium iminodiacetate, sodium maleate, sodium malonate, sodium oxalate, disodium succinate and sodium tartrate; sodium tricarboxylates such as disodium citrate; sodium tetracarboxylates such as disodium ethylenediamine tetraacetate and the like can be exemplified, and organic acid salts including potassium salts thereof and the like can also be used. These salts can be used alone or by combining two or more types thereof.

In particular, from the viewpoint that the magnetic particles having a surface modified with a thermoresponsive polymer or the adsorbent can be aggregated by the addition of a small amount of salts, organic acid salts such as sodium aspartate, disodium citrate, disodium ethylenediamine tetraacetate, sodium glutamate, sodium iminodiacetate, sodium maleate, sodium malonate, sodium oxalate, disodium succinate and sodium tartrate; sulfates such as lithium sulfate, sodium sulfate, potassium sulfate, magnesium sulfate and ammonium sulfate; carbonates such as sodium carbonate and potassium carbonate are preferred.

Further, from the viewpoint that the adsorbent is easily redispersed after aggregation, organic acid salts including sodium monocarboxylates such as sodium acetate; sodium dicarboxylates such as sodium aspartate, sodium glutamate, sodium iminodiacetate, sodium maleate, sodium malonate, sodium oxalate, disodium succinate and sodium tartrate; sodium tricarboxylates such as disodium citrate; sodium tetracarboxylates such as disodium ethylenediamine tetraacetate and the like are preferred, and also potassium salts thereof are preferred.

In order to aggregate the magnetic particles having a surface modified with a thermoresponsive polymer or the adsorbent, for example, an aqueous salt solution may be added to a dispersion of the magnetic particles having a surface modified with a thermoresponsive polymer or the adsorbent to obtain a desired salt concentration.

The necessary amount of the salt to be added for aggregating the magnetic particles having a surface modified with a thermoresponsive polymer or the adsorbent is generally in the range of from 50 mM to 5 M, preferably from 100 to 1000 mM in terms of the final concentration thereof in an aqueous solution though it depends on the type of salt, temperature of the aqueous solution, type of thermoresponsive polymer, concentration of the magnetic particles having a surface modified with a thermoresponsive polymer or the adsorbent or the like.

For example, in the case of an aqueous solution containing 4 mg/mL of the magnetic particles having a surface modified with a thermoresponsive polymer or the adsorbent, by adding one-third volume of a 1 M aqueous salt solution such as a 1 M aqueous sodium sulfate or potassium carbonate solution, the magnetic particles having a surface modified with a thermoresponsive polymer or the adsorbent can be easily aggregated under a condition that the concentration of magnetic particles having a surface modified with a thermoresponsive polymer or the adsorbent is 3 mg/mL, and the salt concentration is 250 mM. Such an aqueous salt solution may be neutralized with an acid or an alkali, or may be dissolved in a buffer or the like for use.

On the other hand, in order to redisperse the aggregated magnetic particles having a surface modified with a thermoresponsive polymer or adsorbent, an aqueous salt solution of a desired concentration may be added, or the salt concentration may be diluted with purified water or the like so that a salt concentration returns to the same concentration as that before dispersion.

(Separation Method and Detection Method of the Present Invention)

In the present invention, separation refers to a procedure in which a substance to be detected is separated and taken out.

The method of separating a substance to be detected from a sample of the present invention is a method comprising the steps of: (1) mixing an adsorbent and the sample in an aqueous solution to adsorb the substance to be detected on the adsorbent, (2) aggregating the adsorbent by changing a salt concentration in the aqueous solution; and (3) collecting the adsorbent by a magnetic force.

The method of detecting a substance to be detected in a sample of the present invention is a method further comprising the step of: (4) detecting the substance to be detected adsorbed on the adsorbent following the steps (1) (2) and (3).

Hereinafter, an example in which an antigen as the substance to be detected is detected and assayed by a sandwich method using a fluorescent dye will be described.

(a) Reagent A containing magnetic particles having a surface modified with a thermoresponsive polymer (an adsorbent) and immobilized with Antibody a against an antigen to be detected and assayed is mixed with a sample containing the antigen which is a substance to be detected to react with each other in a reaction container.

(b) An aqueous solution of a high concentration of a salt (Reagent B) is added and mixed in the reaction mixture to give a salt concentration at which the adsorbent can be aggregated, whereby the adsorbent is aggregated.

(c) The adsorbent is magnetically collected on the wall of the reaction container with a magnet, and a liquid portion containing unnecessary components in the sample is removed. Then, the magnet is removed, and a buffer (Reagent C) is added in such an amount that the adsorbent is dispersed, whereby the adsorbent is redispersed. The same procedure is repeated to wash the adsorbent.

(d) An aqueous solution of a fluorescent dye-labeled Antibody b capable of recognizing a site of the antigen to be detected and assayed different from that of the above-mentioned Antibody a (Reagent D) is added to the resulting adsorbent, and a reaction is allowed to proceed in the reaction container.

(e) The aqueous solution of a high concentration of a salt (Reagent B) is added and mixed in the reaction mixture to give a salt concentration at which the adsorbent can be aggregated, whereby the adsorbent is aggregated.

(f) The adsorbent is magnetically collected on the wall of the reaction container with a magnet, and a liquid portion containing excess components in the Reagent D is removed. Then, the magnet is removed, and the buffer (Reagent C) is added in such an amount that the adsorbent is dispersed, whereby the adsorbent is redispersed. The same procedure is repeated to wash the adsorbent.

(g) The fluorescence intensity of the fluorescent dye is measured.

In this example, a method in which fluorescence is measured using a fluorescent dye-labeled Antibody b capable of recognizing a site of the antigen different from that of the above-mentioned Antibody a as the Reagent D is described, however, any of various methods such as a method in which radioactivity is measured using radiolabeled Antibody b, and a method in which luminescence or color development intensity is measured using Antibody b labeled with an enzyme such as horseradish peroxidase or alkaline phosphatase and a luminescent or color developing reagent which is a substrate for the enzyme can be applied.

The separation method or detection method of the present invention can be preferably used for separation, detection and determination of various substances to be used in the environmental inspection, food inspection, clinical diagnosis or the like.

Specific examples of the substances include pathogenic bacteria in water or food, human immunoglobulin G (IgG), human immunoglobulin M (IgM), human immunoglobulin A (IgA), human immunoglobulin E (IgE), human albumin, human fibrinogen (fibrin and degradation products thereof), α-fetoprotein (AFP), C-reactive protein (CRP), myoglobin, carcinoembryonic antigens, hepatitis virus antigens, human chorionic gonadotropin (hCG), human placental lactogen (hPL), insulin, HIV virus antigens, allergens, bacterial toxins, bacterial antigens, enzymes, hormones, chemical agents and the like in body fluid, urine, sputum, feces and the like.

(Separation Kit and Detection Kit of the Present Invention)

The kit for separating a substance to be separated in a sample of the present invention includes, for example, the following Reagent A, Reagent B and Reagent C.

Reagent A: A dispersion of an adsorbent (particles having a surface modified with a thermoresponsive polymer and immobilized with a ligand)

Reagent B: An aqueous salt solution

Reagent C: A dilution buffer (It is a buffer that can be used for dilution of the above-mentioned Reagents A and B, and for dilution of a sample, and examples thereof include a Tris-HCl buffer, a phosphate buffer and the like.)

Further, the kit for detecting a substance to be detected in a sample of the present invention includes, for example, the following Reagent D, Reagent E and Reagent F in addition to the above-mentioned kit for separating a substance to be separated in a sample (Reagent A, Reagent B and Reagent C).

Reagent D: A solution containing a conjugate of a ligand capable of recognizing a site of a substance to be detected different from that of the ligand in Reagent A with a detection unit (a fluorescent dye, a radioisotope element, an enzyme or the like)

Reagent E: A substrate for an enzyme (in the case where an enzyme is used as the detection unit)

Reagent F: A reference standard for a substance to be detected (as an example, a purified antigen can be used.)

In addition, depending on the type of detection unit, an apparatus for measuring fluorescence intensity, radioactivity intensity, luminescence intensity, color development intensity or the like is needed.

EXAMPLES

Hereinafter, the present invention will be described in further detail with reference to Examples, however, the present invention is not limited to these Examples.

Production Example 1

Preparation Method of Magnetic Particles (60 nm)

In a 100 mL flask, 3 mL of a mixed aqueous solution of ferric chloride hexahydrate (1.0 mol) and ferrous chloride tetrahydrate (0.5 mol) and 60 mL of an aqueous solution of 10% by weight of dextran (manufactured by Wako Pure Chemicals Industries, Ltd., molecular weight of 32000 to 40000), which is a polyhydric alcohol, were placed, and the mixed aqueous solution was stirred using a mechanical stirrer. After the temperature of this mixed aqueous solution was raised to 50° C., 5.0 mL of an aqueous solution of 25% by weight of ammonia was added dropwise thereto, and the mixed aqueous solution was stirred for about 1 hour. By this procedure, dextran-containing magnetic particles having an average particle size of about 60 nm were obtained (In the production example, reference was made to JP-A-2005-82538).

Production Example 2

Preparation Method of Biotin Monomer (N-biotinyl-N'-methacryloyltrimethyleneamide)

18 g of N-(3-aminopropyl)methacrylamide hydrochloride, 24 g of biotin and 30 g of triethylamine were dissolved in 300 mL of N,N-dimethylformamide (DMF) and the resulting mixture was cooled to 0° C. A solution obtained by dissolving 28 g of diphenylphosphanylazide in 50 mL of DMF was added dropwise to this mixture over 1 hour. After completion of dropwise addition, the mixture was stirred at 0° C. for 3 hours, and stirred at room temperature for an additional 12 hours. Thereafter, the solvent was distilled off under reduced pressure, and the residue was purified by column chromatography using a mixed solvent of chloroform and methanol as a developing solvent, whereby 22 g of white powder was obtained. This was a target substance, N-biotinyl-N'-methacryloyltrimethyleneamide, (yield: 59%).

Production Example 3

Preparation Method of LCST-type Magnetic Particles on which Biotin has been Immobilized as a Ligand In a 50 ml three-neck flask, 300 mg of N-isopropylacrylamide, 3 mg of the biotin monomer prepared by the above-mentioned method and 2 mL of an aqueous solution of 2% by weight of the dextran-containing magnetic particles (60 nm) prepared by the above-mentioned method were placed, and the final volume was made up to 20 mL with distilled water. After the aqueous solution was subjected to nitrogen replacement, 200 µL of a 0.2 M cerium(IV) diammonium nitrate solution was further added thereto, and a reaction was allowed to proceed with stirring for 2 hours, whereby LCST-type magnetic particles were obtained. The average particle size of the thus obtained LCST-type magnetic particles was measured using a laser zeta potential meter, ELS-8000 manufactured by Otsuka Electronics Co. Ltd., and it was found to be about 100 nm. These particles had an LCST of 37° C., and completely dispersed and were difficult to be collected with a magnet in an aqueous solution at a temperature lower than the LCST. However, when the temperature of the aqueous solution was raised to the LCST or higher, the particles immediately aggregated and could be easily collected with a magnet.

Test Example 1

Experimental Example of Addition of a Salt to Magnetic Particles and Magnetic Collection Thereof An aqueous dispersion containing 0.4% by weight of the dextran-containing magnetic particles prepared by the above-mentioned method and an aqueous dispersion containing 0.4% by weight of the LCST-type magnetic particles prepared by the above-mentioned method were prepared in an amount of 100 µL each, and 25 µL of a 1 M $Na_2SO_4$ aqueous solution was added thereto at a constant temperature of 30° C. such that the final concentration of $Na_2SO_4$ was 200 mM. The dextran-containing magnetic particles were in a completely dispersed state even after addition of the $Na_2SO_4$ aqueous solution, and could not be magnetically collected. On the other hand, the LCST-type magnetic particles aggregated after addition of the $Na_2SO_4$ aqueous solution and could be magnetically collected within 1 minute. When $H_2O$ was added to the magnetically collected LCST-type magnetic particles, the particles were redispersed.

As described above, the LCST-type magnetic particles which were subjected to surface modification with a thermoresponsive polymer could be magnetically separated when the final concentration of $Na_2SO_4$ was 200 mM, however, the dextran-containing magnetic particles which were not subjected to surface modification with a thermoresponsive polymer could not be magnetically separated when the final concentration of $Na_2SO_4$ was 200 mM.

Example 1

An example in which an effect of salt concentration on aggregation and dispersion of LCST-type magnetic particles was studied will be described.

In this connection, the magnetic particles prepared in the above-mentioned Production example 1 were used as the magnetic particles which were not subjected to surface modification with a thermoresponsive polymer, and the LCST-type magnetic particles on which biotin was immobilized prepared in the above-mentioned Production example 3 were used as the adsorbent.

In a 1.5 mL microtube, each of the aqueous salt solutions shown in Table 1 and Table 3 was added to 100 µL of an aqueous dispersion of 0.4% by weight of the above-mentioned LCST-type magnetic particles to give a desired final concentration, followed by mixing by pipetting. Then, the mixture was left stand at 30° C. for 30 seconds, and aggregation was visually observed (Tables 1 and 3).

The microtube containing a sample, in which aggregation was observed, was placed on a stand with a magnet (Magna-Stand 6 manufactured by Magnabeat Inc.) and magnetic separation was carried out at 30° C. for 1 minute, and the supernatant was removed. 100 µL of purified water (water obtained by purification using Direct-Q (trade name) manufactured by Millipore) was added to the residue, and redispersion thereof was confirmed.

Comparative Example 1

The same procedure as in Example was carried out except that magnetic particles which were not subjected to surface modification with a thermoresponsive polymer and prepared in Production example 1 were used in place of the LCST-type magnetic particles, and aggregation was visually observed. As a result, aggregation could not be observed (Table 2 and Table 4).

The results are shown in Table 1 to Table 4. It was found that the LCST-type magnetic particles could allow the adsorbent to be aggregated and separated by adjusting a salt concentration using any of various aqueous salt solutions, while the magnetic particles which were not subjected to surface modification with a thermoresponsive polymer could not allow the adsorbent to be aggregated or separated even by adjusting a salt concentration using any of various aqueous salt solutions.

TABLE 1

| Type of salt | Salt concentration | | | | |
|---|---|---|---|---|---|
| | 100 mM | 200 mM | 300 mM | 400 mM | 500 mM |
| $Na_2SO_4$ | ◯ | ◯ | ◯ | ◯ | ◯ |
| $(NH_4)_2SO_4$ | X | ◯ | ◯ | ◯ | ◯ |
| $MgSO_4$ | X | ◯ | ◯ | ◯ | ◯ |
| $Na_2SO_3$ | ◯ | ◯ | ◯ | ◯ | ◯ |
| $Na_2CO_3$ | ◯ | ◯ | ◯ | ◯ | ◯ |
| $K_2CO_3$ | ◯ | ◯ | ◯ | ◯ | ◯ |
| $NiSO_4$ | X | ◯ | ◯ | ◯ | ◯ |
| $NiCl_2$ | X | X | ◯ | ◯ | ◯ |
| $CoCl_2$ | X | X | ◯ | ◯ | ◯ |
| $NaHCO_3$ | X | X | ◯ | ◯ | ◯ |
| NaCl | X | X | ◯ | ◯ | ◯ |

◯: Aggregation and dispersion could be observed.
X: Aggregation could not be observed.

TABLE 2

| Type of salt | Salt concentration | | | | |
|---|---|---|---|---|---|
| | 100 mM | 200 mM | 300 mM | 400 mM | 500 mM |
| $Na_2SO_4$ | X | X | X | X | X |
| $(NH_4)_2SO_4$ | X | X | X | X | X |
| $MgSO_4$ | X | X | X | X | X |
| $Na_2SO_3$ | X | X | X | X | X |
| $Na_2CO_3$ | X | X | X | X | X |
| $K_2CO_3$ | X | X | X | X | X |
| $NiSO_4$ | X | X | X | X | X |
| $NiCl_2$ | X | X | X | X | X |
| $CoCl_2$ | X | X | X | X | X |
| $NaHCO_3$ | X | X | X | X | X |
| NaCl | X | X | X | X | X |

◯: Aggregation and dispersion could be observed.
X: Aggregation could not be observed.

TABLE 3

| Type of salt | Final Salt concentration | | | | |
|---|---|---|---|---|---|
| | 100 mM | 200 mM | 300 mM | 400 mM | 500 mM |
| Sodium acetate | X | X | ◯ | ◯ | ◯ |
| Sodium aspartate | ◯ | ◯ | ◯ | ◯ | ◯ |
| Disodium citrate | ◯ | ◯ | ◯ | ◯ | ◯ |
| Disodium ethylenediamine tetraacetate | ◯ | ◯ | ◯ | ◯ | ◯ |
| Sodium glutamate | ◯ | ◯ | ◯ | ◯ | ◯ |
| Sodium iminodiacetate | ◯ | ◯ | ◯ | ◯ | ◯ |
| Sodium maleate | ◯ | ◯ | ◯ | ◯ | ◯ |
| Sodium malonate | ◯ | ◯ | ◯ | ◯ | ◯ |
| Sodium oxalate | ◯ | ◯ | ◯ | ◯ | ◯ |
| Disodium succinate | ◯ | ◯ | ◯ | ◯ | ◯ |
| Sodium tartrate | ◯ | ◯ | ◯ | ◯ | ◯ |

◯: Aggregation and dispersion could be observed.
X: Aggregation could not be observed.

TABLE 4

| Type of salt | Final Salt concentration | | | | |
|---|---|---|---|---|---|
| | 100 mM | 200 mM | 300 mM | 400 mM | 500 mM |
| Sodium acetate | X | X | X | X | X |
| Sodium aspartate | X | X | X | X | X |
| Disodium citrate | X | X | X | X | X |
| Disodium ethylenediamine tetraacetate | X | X | X | X | X |
| Sodium glutamate | X | X | X | X | X |
| Sodium iminodiacetate | X | X | X | X | X |
| Sodium maleate | X | X | X | X | X |
| Sodium malonate | X | X | X | X | X |
| Sodium oxalate | X | X | X | X | X |
| Disodium succinate | X | X | X | X | X |
| Sodium tartrate | X | X | X | X | X |

○: Aggregation and dispersion could be observed.
X: Aggregation could not be observed.

Example 2

An example in which TSH (thyroid-stimulating hormone) was determined by a sandwich method using an antibody bound to magnetic particles having a surface modified with a thermoresponsive polymer and an antibody bound to alkaline phosphatase will be described.

2 μL of a biotinylated anti-TSH-α antibody (an antibody obtained by biotinylating a mouse anti-TSH-α antibody manufactured by Leinco Technologies, Inc. (biotinylation was performed by Asahi Techno Glass), concentration: 0.75 mg/mL), 0.5 μL of an alkaline phosphatase-binding anti-TSH-β antibody (an antibody obtained by binding alkaline phosphatase to a mouse anti-TSH-β antibody manufactured by Leinco Technologies, Inc. (binding of alkaline phosphatase was performed by Asahi Techno Glass), concentration: 1.09 mg/mL), 12.5 μL of a TBS buffer (20 mM Tris-HCl (pH 7.5), 150 mM NaCl), and 20 μL of magnetic particles having a surface modified with a thermoresponsive polymer (Therma-Max (registered trademark) LA Avidin manufactured by Magnabeat Inc., concentration: 4 mg/mL) were mixed at this ratio and a necessary amount thereof was prepared. The thus prepared mixture was dispensed into microtubes in an amount of 35 μL each (2 series). To each of the microtubes, 65 μL of Architect (registered trademark) TSH calibrator (manufactured by Abbot Japan) was added such that the concentration of TSH was 0 μIU/mL, 4.0 μIU/mL or 40.0 μIU/mL, followed by mixing by pipetting, and a reaction was allowed to proceed at room temperature for 1 minute. After completion of the reaction, 30 μL of a 1 M sodium sulfate solution was added to the reaction mixture (total salt concentration: 268 mM), followed by mixing by pipetting. After a reaction was allowed to proceed at 30° C. for 30 seconds, the microtubes were placed on a stand with a magnet (Magna-Stand 6 (trade name) manufactured by Magnabeat Inc.) and magnetic separation was carried out at 30° C. for 1 minute, and the supernatant was removed. Then, 100 μL of a TBS-T buffer (20 mM Tris-HCl (pH 7.5), 150 mM NaCl, 0.05% (w/v) Tween 20) was added to the residue to redisperse it, and 30 μL of a 1 M sodium sulfate solution was added thereto (total salt concentration: 380 mM), followed by mixing by pipetting. After a reaction was allowed to proceed at 30° C. for 30 seconds, magnetic separation was carried out at 30° C. for 1 minute, followed by washing. The washing was carried out by the same procedure as above and repeated twice. Finally, the pellet was redispersed in 100 μL of a TBS buffer, and 100 μL of a luminescent substrate (Lumigen (registered trademark) APS-5 manufactured by Lumigen Inc.) was added thereto, and the mixture was stirred for 5 seconds. Then, a reaction was allowed to proceed for 10 seconds, and a luminescence intensity was measured for 0.1 second using a multilabel plate reader (Mithras LB940, a multilabel plate reader manufactured by Berthold Japan).

Figure 1:
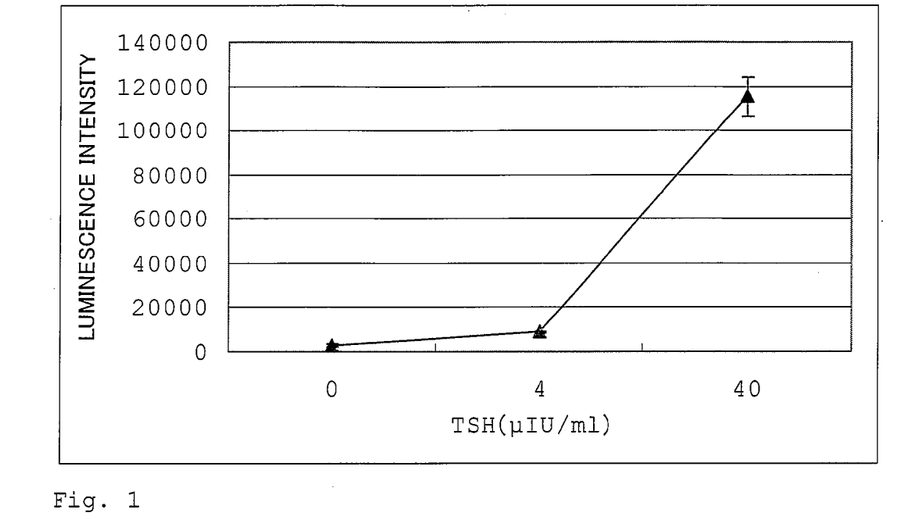
FIG. 1 is a graph showing the results of detection and measurement of the concentration of TSH by the method (sodium sulfate was used as a salt) of the present invention (N=2; represented by an average value).

The results of measurement of luminescence intensity are shown in Table 5 and FIG. 1. According to Table 5 and FIG. 1, it was found that the luminescence intensity changed in proportion to the concentration of TSH. That is, it was found that by using the present method, TSH could be detected and the concentration thereof could be determined favorably under a given condition of a temperature of 30° C.

TABLE 5

| TSH (μIU/mL) | 1 | 2 |
|---|---|---|
| 0 | 2196 | 3589 |
| 4 | 8604 | 9082 |
| 40 | 106412 | 124103 |

Example 3

An example in which TSH (thyroid-stimulating hormone) was determined by a sandwich method using an antibody bound to magnetic particles having a surface modified with a thermoresponsive polymer and an antibody bound to alkaline phosphatase will be described.

0.2 μL of a biotinylated anti-TSH-α antibody (an antibody obtained by biotinylating a mouse anti-TSH-α antibody manufactured by Leinco Technologies, Inc. (biotinylation was performed by Asahi Techno Glass), concentration: 0.75 mg/mL), 0.2 μL of an alkaline phosphatase-binding anti-TSH-β antibody (an antibody obtained by binding alkaline phosphatase to a mouse anti-TSH-β antibody manufactured by Leinco Technologies, Inc. (binding of alkaline phosphatase was performed by Asahi Techno Glass), concentration: 1.09 mg/mL), 12.5 μL of a TBS buffer (20 mM Tris-HCl (pH 7.5), 150 mM NaCl), and 20 μL of magnetic particles having a surface modified with a thermoresponsive polymer (Therma-Max (registered trademark) LA Avidin manufactured by Magnabeat Inc., concentration: 4 mg/mL) were mixed at this ratio and a necessary amount thereof was prepared. The thus prepared mixture was dispensed into microtubes in an amount of 35 μL each (2 series). To each of the microtubes, 65 μL of a TSH solution (Lumipulse (registered trademark) manufactured by Fujirebio Inc., TSH-N standard TSH solution (WHO Standard, 2nd International Standard)) was added such that the concentration of TSH was 0 μIU/mL, 5.0 μIU/mL, 60.0 μIU/mL or 200.0 μIU/mL, followed by mixing by pipetting, and a reaction was allowed to proceed at room temperature for 5 minutes. After completion of the reaction, 30 μL of a 1 M sodium tartrate solution was added to the reaction mixture (total salt concentration: 268 mM), followed by mixing by pipetting. After a reaction was allowed to proceed at 30° C. for 30 seconds, the microtubes were placed on a stand with a magnet (Magna-Stand 6 (trade name) manufactured by Magnabeat Inc.) and magnetic separation was carried out at 30° C. for 1 minute, and the supernatant was removed. Then, 100 μL of a TBS-T buffer (20 mM Tris-HCl (pH 7.5), 150 mM NaCl, 0.05% (w/v) Tween 20) was added to the residue to redisperse it, and 30 μL of a 1 M sodium tartrate solution was added thereto (total salt concentration: 380 mM), followed by mixing by pipetting. After a reaction was allowed to proceed at 30° C. for 30 seconds, magnetic separation was carried out at 30° C. for 1 minute, followed by washing. The washing was carried out by the same procedure as above and repeated twice. Finally, the pellet was redispersed in 100 μL of a TBS buffer, and 100 μL of a luminescent substrate (Lumigen (registered trademark) APS-5 manufactured by Lumigen Inc.) was added thereto, and the mixture was stirred for 5 seconds. Then, a reaction was allowed to proceed for 10 seconds, and a luminescence intensity was measured for 0.1 second using a multilabel plate reader (Mithras LB940, a multilabel plate reader manufactured by Berthold Japan).

Figure 2:
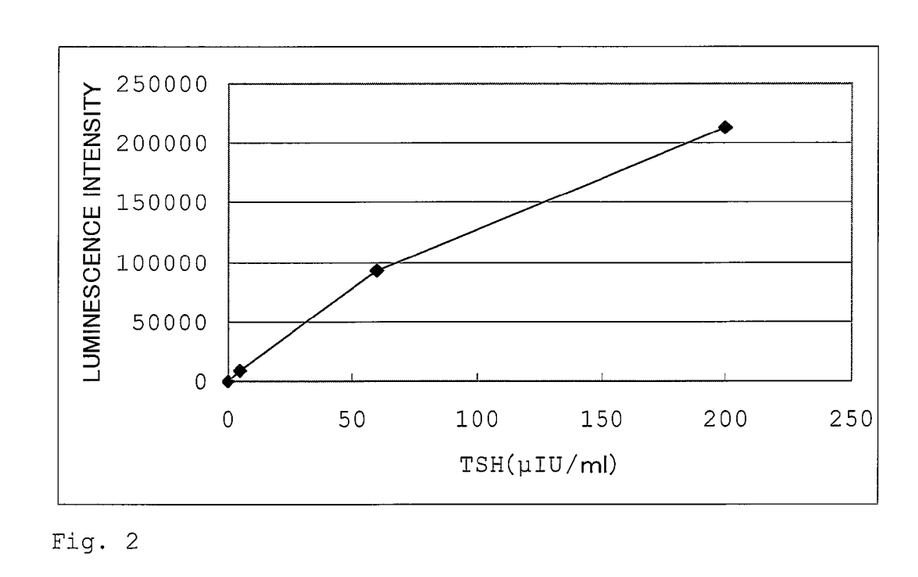
FIG. 2 is a graph showing the results of detection and measurement of the concentration of TSH by the method (sodium tartrate was used as a salt) of the present invention (N=2; represented by an average value).

The results of measurement of luminescence intensity are shown in Table 6 and FIG. 2. According to Table 6 and FIG. 2, it was found that the luminescence intensity changed in proportion to the concentration of TSH. That is, it was found that by using the present method, TSH could be detected and the concentration thereof could be determined favorably under a given condition of a temperature of 30° C.

TABLE 6

| TSH (μIU/mL) | 1 | 2 |
|---|---|---|
| 0 | 449 | 335 |
| 5 | 9469 | 8831 |
| 60 | 96182 | 89915 |
| 200 | 213702 | 213035 |

Example 4

By using the same method as in Example 2 or Example 3, human immunoglobulin G, human immunoglobulin M, human immunoglobulin A, human immunoglobulin E, human albumin, human fibrinogen (fibrin and degradation products thereof), α-fetoprotein (AFP), C-reactive protein (CRP), myoglobin, carcinoembryonic antigens, hepatitis virus antigens, human chorionic gonadotropin (hCG), human placental lactogen (hPL), insulin, HIV virus antigens, allergens, bacterial toxins, bacterial antigens, enzymes, hormones, chemical agents and the like in body fluid, urine, sputum, feces and the like can be assayed.

Example 5

An example in which a study in which redispersion could be achieved in a short time when a carboxylate was used was performed will be described.

In microtubes, 100 μL of an aqueous dispersion of 0.4% by weight of the LCST-type magnetic particles prepared in the above-mentioned Production example 3 was left stand at 42° C. for 30 seconds thereby aggregating the particles. Subsequently, each microtube was placed on a stand with a magnet (Magna-Stand 6 (trade name) manufactured by Magnabeat Inc.) and magnetic separation was carried out at 42° C. until the supernatant became clear. The time required for magnetic separation at this time was 60 seconds. Thereafter, the supernatant was removed, and 100 μL of purified water (water obtained by purification using Direct-Q (trade name) manufactured by Millipore) was added to the residue, followed by mixing by pipetting to redisperse the residue. The time required for redispersion at this time was 60 seconds.

In a similar manner, to 100 μL of an aqueous dispersion of 0.4% by weight of the LCST-type magnetic particles on which biotin was immobilized prepared in the above-mentioned Production example 3, sodium sulfate, sodium sulfite or sodium citrate was added to give a final concentration of the respective compounds shown in Table 7, followed by mixing by pipetting. Then, the mixture was left stand at 30° C. for 30 seconds thereby aggregating the particles. Subsequently, the microtubes were placed on Magna-Stand 6, and magnetic separation was carried out at 30° C. until the supernatant became clear. The time required for magnetic separation at this time is shown in Table 7. Then, the supernatant was removed, and 100 μL of purified water was added to the residue, followed by mixing by pipetting, and the time required for redispersion was measured.

The results are shown in Table 7. In the case where aggregation and magnetic separation were carried out by raising the temperature of the mixture to 42° C. without adding a salt, the time required for redispersion was 60 seconds. In the case where the same procedure was carried out at 30° C. using sodium sulfate and sodium sulfite, the time required for redispersion was 60 seconds. On the other hand, in the case where the same procedure was carried out at 30° C. using sodium citrate, which is a carboxylate, the time required for redispersion was 30 seconds. From the results, it was indicated that when a carboxylate was used, redispersion could be achieved at short time.

TABLE 7

| Type of salt | Final salt concentration | Aggregation at 30° C. (sec) | Time required for magnetic separation (sec) | Time required for redispersion (sec) |
|---|---|---|---|---|
| Sodium sulfate | 100 mM | 30 | 60 | 60 |
| | 200 mM | 30 | 60 | 60 |
| | 300 mM | 30 | 30 | 60 |
| Sodium sulfite | 100 mM | 30 | 60 | 60 |
| | 200 mM | 30 | 60 | 60 |
| | 300 mM | 30 | 30 | 60 |
| Sodium citrate | 100 mM | 30 | 60 | 30 |
| | 200 mM | 30 | 30 | 30 |
| | 300 mM | 30 | 30 | 30 |

While the invention has been described in detail with reference to preferred embodiments thereof, it will be apparent to one skilled in the art that various changes can be made, and equivalents employed, without departing from the scope of the invention. All the references cited herein, including the priority documents, JP 2007-173469 and JP 2008-028641, are incorporated as a part of this application by reference.

What is claimed is:

1. A method of separating a substance to be detected from a sample, comprising the steps of:
    mixing an adsorbent and the sample in an aqueous solution to adsorb the substance to be detected on the adsorbent,
    aggregating the adsorbent by changing a salt concentration in the aqueous solution at a given temperature without heating or cooling the aqueous solution; and collecting the adsorbent from the aqueous solution by a magnetic force, wherein said adsorbent comprises a magnetic particle of an average particle size of 50 to 1000 nm, a surface of which is modified with a thermoresponsive polymer and is immobilized with a substance having an affinity for the substance to be detected.

2. The method according to claim 1, wherein the thermoresponsive polymer is a polymer obtained by polymerization of at least one type of monomer selected from the group consisting of N-n-propylacrylamide, N-isopropylacrylamide, N-t-butylacrylamide, N-ethylacrylamide, N,N-dimethylacrylamide, N-acryloylpyrrolidine, N-acryloylpiperidine, N-acryloylmorpholine, N-n-propylmethacrylamide, N-isopropylmethacrylamide, N-ethylmethacrylamide, N,N-dimethylmethacrylamide, N-methacryloylpyrrolidine, N-methacryloylpiperidine and N-methacryloylmorpholine.

3. The method according to claim 1, wherein the thermoresponsive polymer is a polymer obtained by polymerization of at least one type of monomer selected from the group consisting of N-acryloylglycinamide, N-acryloylnipecotamide and N-acryloylasparaginamide.

4. The method according to claim 1, wherein the average particle size of the magnetic particle is from 50 to 200 nm.

5. The method according to claim 1, wherein the salt contains at least one type of compound selected from the group consisting of lithium sulfate, sodium sulfate, potassium sulfate, magnesium sulfate, ammonium sulfate, sodium carbonate and potassium carbonate.

6. The method according to claim 1, wherein the salt contains at least one type of compound selected from the group consisting of a sodium monocarboxylate, a potassium monocarboxylate, a sodium dicarboxylate, a potassium dicarboxylate, a sodium tricarboxylate, a potassium tricarboxylate, a sodium tetracarboxylate and a potassium tetracarboxylate.

7. The method according to claim 6, wherein the salt contains at least one type of compound selected from the group consisting of sodium acetate, sodium aspartate, disodium citrate, disodium ethylenediamine tetraacetate, sodium glutamate, sodium iminodiacetate, sodium maleate, sodium malonate, sodium oxalate, disodium succinate and sodium tartrate.

8. A kit for separating or detecting a substance to be detected in a sample, comprising an adsorbent and an aqueous salt solution but no heating or cooling means, wherein said adsorbent comprises a magnetic particle of an average particle size of 50 to 1000 nm, a surface of which is modified with a thermoresponsive polymer and is immobilized with a substance having an affinity for the substance to be detected.

9. A method of aggregating or dispersing magnetic particles, comprising the step of aggregating or dispersing magnetic particles having a surface modified with a thermoresponsive polymer, which are obtained by subjecting magnetic particles to surface modification with a thermoresponsive polymer, by changing a salt concentration in an aqueous solution at a given temperature without heating or cooling the aqueous solution.

10. The method according to claim 9, wherein the magnetic particle having a surface modified with a thermoresponsive polymer has a substance having an affinity for a substance to be detected on its surface.

11. A method of detecting a substance to be detected in a sample, comprising the steps of:
   separating the substance to be detected from the sample by adsorbing the substance to be detected on the adsorbent by the method according to claim 1; and
   detecting the substance to be detected adsorbed on the adsorbent.

* * * * *